(12) United States Patent
Heiliger

(10) Patent No.: US 11,246,648 B2
(45) Date of Patent: Feb. 15, 2022

(54) SURGICAL FORCEPS WITH BILATERAL AND UNILATERAL JAW MEMBERS

(71) Applicant: COVIDIEN LP, Mansfield, MA (US)

(72) Inventor: Zachary S. Heiliger, Nederland, CO (US)

(73) Assignee: COVIDIEN LP, Mansfield, MA (US)

( * ) Notice: Subject to any disclaimer, the term of this patent is extended or adjusted under 35 U.S.C. 154(b) by 650 days.

(21) Appl. No.: 16/214,358

(22) Filed: Dec. 10, 2018

(65) Prior Publication Data

US 2020/0179038 A1 Jun. 11, 2020

(51) Int. Cl.
*A61B 18/14* (2006.01)
*A61B 17/29* (2006.01)
(Continued)

(52) U.S. Cl.
CPC .. *A61B 18/1447* (2013.01); *A61B 2017/2925* (2013.01); *A61B 2017/2936* (2013.01);
(Continued)

(58) Field of Classification Search
CPC ........ A61B 18/1447; A61B 2017/2925; A61B 2017/2936; A61B 2017/2938; A61B 2017/2944; A61B 2017/2947; A61B 2018/0063; A61B 2018/126; A61B 2018/1455; A61B 2017/2926;
(Continued)

(56) References Cited

U.S. PATENT DOCUMENTS

D249,549 S 9/1978 Pike
D263,020 S 2/1982 Rau, III
(Continued)

FOREIGN PATENT DOCUMENTS

CA 2741309 A1 * 12/2011 ............. A61B 17/29
CN 201299462 Y 9/2009
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
(Continued)

*Primary Examiner* — Linda C Dvorak
*Assistant Examiner* — Mystee Nguyen Delgado
(74) *Attorney, Agent, or Firm* — Carter, DeLuca & Farrell LLP

(57) ABSTRACT

An endoscopic bipolar forceps includes a housing having a shaft extending therefrom with an end effector disposed at a distal end thereof. The end effector assembly includes a first and second jaw members having cam slots defined therein with distal and proximal sections at different angles relative to a longitudinal axis. Upon initial actuation of a handle, a cam pin engages the distal cam section of the first jaw member causing it to move relative to the second jaw member while the second jaw member remains stationary. Upon continued actuation of the handle, the cam pin engages the proximal cam section of the first jaw member causing the first jaw member to remain stationary while the second jaw member cams relative to the first jaw member to close against tissue disposed between the first and second jaw members.

14 Claims, 5 Drawing Sheets

(51) Int. Cl.
*A61B 18/12* (2006.01)
*A61B 18/00* (2006.01)

(52) U.S. Cl.
CPC .............. *A61B 2017/2938* (2013.01); *A61B 2017/2944* (2013.01); *A61B 2017/2947* (2013.01); *A61B 2018/0063* (2013.01); *A61B 2018/126* (2013.01); *A61B 2018/1455* (2013.01)

(58) Field of Classification Search
CPC ....... A61B 18/085; A61B 17/28; A61B 17/29; A61B 2017/2901; A61B 18/1442; A61B 2017/320094; A61B 2017/320078; A61M 25/0067
See application file for complete search history.

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 4,887,612 A * | 12/1989 | Esser | A61B 10/06 600/564 |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| 6,083,150 A * | 7/2000 | Aznoian | A61B 10/06 600/564 |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 9,084,608 B2 | 7/2015 | Larson et al. | |
| 9,211,657 B2 | 12/2015 | Ackley et al. | |
| 2012/0022584 A1 * | 1/2012 | Donnigan | A61B 18/1445 606/206 |
| 2012/0065466 A1 * | 3/2012 | Slater | A61B 17/295 600/104 |
| 2012/0172924 A1 * | 7/2012 | Allen, IV | A61B 17/29 606/205 |
| 2014/0221995 A1 | 8/2014 | Guerra et al. | |
| 2014/0221999 A1 | 8/2014 | Cunningham et al. | |
| 2014/0228842 A1 | 8/2014 | Dycus et al. | |
| 2014/0230243 A1 | 8/2014 | Roy et al. | |
| 2014/0236149 A1 | 8/2014 | Kharin et al. | |
| 2014/0243811 A1 | 8/2014 | Reschke et al. | |
| 2014/0243824 A1 | 8/2014 | Gilbert | |
| 2014/0249528 A1 | 9/2014 | Hixson et al. | |
| 2014/0250686 A1 | 9/2014 | Hempstead et al. | |
| 2014/0257274 A1 | 9/2014 | McCullough, Jr. et al. | |
| 2014/0257283 A1 | 9/2014 | Johnson et al. | |
| 2014/0257284 A1 | 9/2014 | Artale | |
| 2014/0257285 A1 | 9/2014 | Moua | |
| 2014/0276803 A1 | 9/2014 | Hart | |
| 2014/0284313 A1 | 9/2014 | Allen, IV et al. | |
| 2014/0288549 A1 | 9/2014 | McKenna et al. | |
| 2014/0288553 A1 | 9/2014 | Johnson et al. | |
| 2014/0330308 A1 | 11/2014 | Hart et al. | |
| 2014/0336635 A1 | 11/2014 | Hart et al. | |
| 2014/0353188 A1 | 12/2014 | Reschke et al. | |
| 2015/0018816 A1 | 1/2015 | Latimer | |
| 2015/0025528 A1 | 1/2015 | Arts | |
| 2015/0032106 A1 | 1/2015 | Rachlin | |
| 2015/0051598 A1 | 2/2015 | Orszulak et al. | |
| 2015/0051640 A1 | 2/2015 | Twomey et al. | |
| 2015/0066026 A1 | 3/2015 | Hart et al. | |
| 2015/0080880 A1 | 3/2015 | Sartor et al. | |
| 2015/0080889 A1 | 3/2015 | Cunningham et al. | |
| 2015/0082928 A1 | 3/2015 | Kappus et al. | |
| 2015/0088122 A1 | 3/2015 | Jensen | |
| 2015/0088126 A1 | 3/2015 | Duffin et al. | |
| 2015/0088128 A1 | 3/2015 | Couture | |
| 2015/0094714 A1 | 4/2015 | Lee et al. | |
| 2020/0367921 A1 * | 11/2020 | Basu | A61B 17/29 |

FOREIGN PATENT DOCUMENTS

| | | |
|---|---|---|
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |

(56) References Cited

FOREIGN PATENT DOCUMENTS

| | | |
|---|---|---|
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 | 9/1984 |
| JP | 61501086 | 9/1984 |
| JP | 1024051 A | 1/1989 |
| JP | 1147150 A | 6/1989 |
| JP | 6502328 | 3/1992 |
| JP | 55106 | 1/1993 |
| JP | H0540112 A | 2/1993 |
| JP | 6121797 A | 5/1994 |
| JP | S121797 A | 5/1994 |
| JP | 6285078 A | 10/1994 |
| JP | 6511401 | 12/1994 |
| JP | H06343644 A | 12/1994 |
| JP | H07265328 A | 10/1995 |
| JP | 08056955 | 3/1996 |
| JP | 08252263 A | 10/1996 |
| JP | 8289895 A | 11/1996 |
| JP | 8317934 A | 12/1996 |
| JP | 8317936 A | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.

(56) References Cited

OTHER PUBLICATIONS

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler, Abandoned.
U.S. Appl. No. 09/177,950, filed Oct. 23, 1998; inventor: Randel A. Frazier, abandoned.
U.S. Appl. No. 09/387,883, filed Sep. 1, 1999; inventor: Dale F. Schmaltz, abandoned.
U.S. Appl. No. 09/591,328, filed Jun. 9, 2000; inventor: Thomas P. Ryan, abandoned.
U.S. Appl. No. 12/336,970, filed Dec. 17, 2008; inventor: Paul R. Sremeich, abandoned.
U.S. Appl. No. 14/065,644, filed Oct. 29, 2013; inventor: Reschke, abandoned.
Heniford et al. "Initial Research and Clinical Results with an Electrothermal Bipolar Vessel Sealer" Oct. 1999.

\* cited by examiner

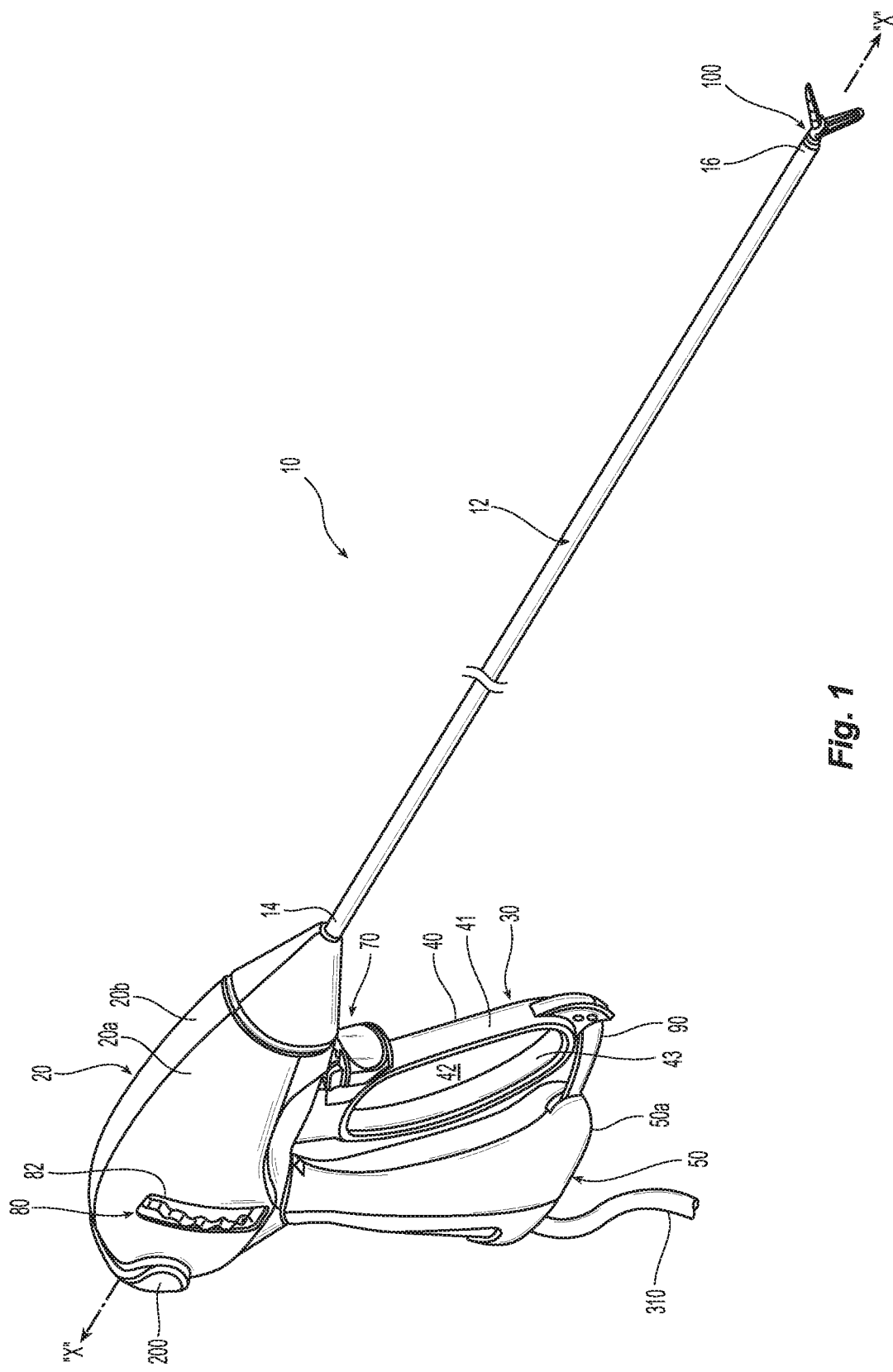

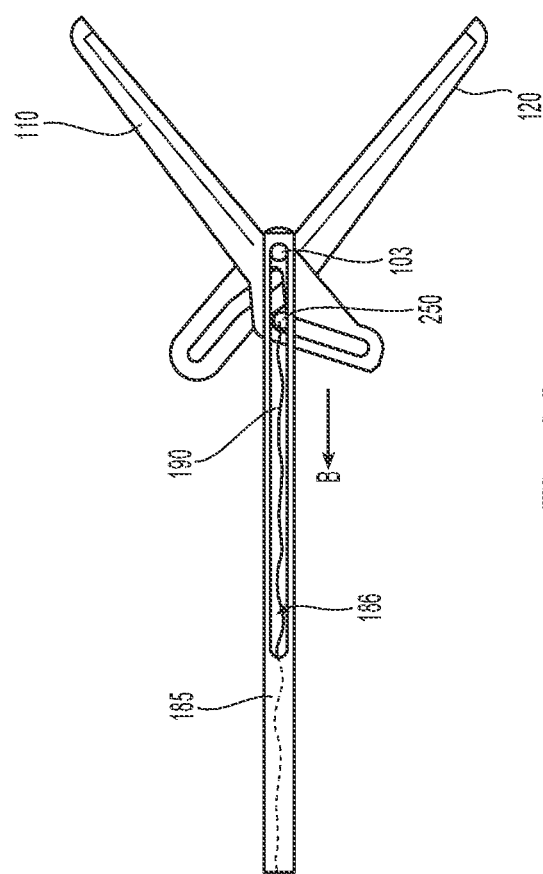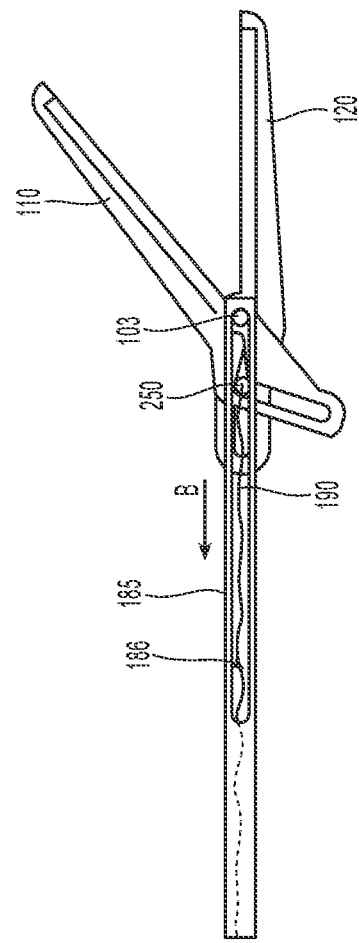

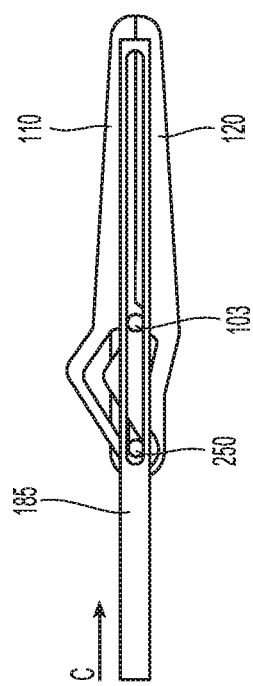

SURGICAL FORCEPS WITH BILATERAL AND UNILATERAL JAW MEMBERS

BACKGROUND

The present disclosure relates to an electrosurgical forceps and more particularly, the present disclosure relates to an endoscopic bipolar electrosurgical forceps for sealing and/or cutting tissue having jaw members that move in both a bilateral and unilateral manner.

TECHNICAL FIELD

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

Endoscopic forceps can be unilateral meaning than only one jaw member moves relative to the other jaw member to grasp tissue or bilateral meaning that both jaw members move relative to one another to grasp tissue. In some instances it is advantageous to utilize a unilateral jaw member arrangement and in other circumstances it is advantageous to utilize a bilateral jaw member arrangement.

SUMMARY

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

In accordance with aspects of the present disclosure, an endoscopic bipolar forceps includes a housing having a shaft extending from the housing including an end effector assembly disposed at a distal end thereof and defining a longitudinal axis defined therethrough. The end effector assembly includes a first jaw member having a cam slot defined therein including a distal cam section and a proximal cam section. The distal cam section is disposed at a first angle relative to the longitudinal axis and the proximal cam section is disposed at a different angle relative to the longitudinal axis. The end effector assembly also includes a second jaw member having a cam slot defined therein including a distal cam section and a proximal cam section. The distal cam section is disposed at a first angle relative to the longitudinal axis and the proximal cam section is disposed at a different angle relative to the longitudinal axis.

A pivot is operably coupled to the first and second jaw members to facilitate pivotable motion therebetween. A movable handle is operably coupled to a drive rod configured to translate a cam pin within the cam slots of the first and second jaw members. Upon initial actuation of the movable handle relative to the housing, the cam pin engages the distal cam section of the first jaw member causing the first jaw member to move relative to the second jaw member about the pivot while the cam pin engages the distal cam section of the second jaw member causing the second jaw member to remain stationary. Upon continued actuation of the movable handle relative to the housing, the cam pin engages the proximal cam section of the first jaw member causing the first jaw member to remain stationary relative to the second jaw member while the cam pin engages the proximal cam section of the second jaw member causing the second jaw member to move relative to the first jaw member about the pivot to close against tissue disposed between the first and second jaw members.

In aspects according to the present disclosure, upon initial actuation of the movable handle, the first jaw member is moved from a bilateral jaw position to a unilateral jaw position. In other aspects according to the present disclosure, when the second jaw member is disposed in the initial bilateral position, the distal cam section of the second jaw member is substantially parallel to the longitudinal axis. In still other aspects according to the present disclosure, when the first jaw member is disposed in the unilateral position, the proximal cam section of the first jaw member is substantially parallel to the longitudinal axis.

In aspects according to the present disclosure, actuation of the movable handle pulls the cam pin proximally. In yet other aspects according to the present disclosure, the first jaw member includes a tissue engaging surface and the distal cam section of the first jaw member is disposed at an angle within the range of about 0 degrees to about 90 degrees relative to the tissue engaging surface. In still other aspects according to the present disclosure, the proximal cam section of the first jaw member is disposed at an angle within the range of about 0 degrees to about 90 degrees relative to the tissue engaging surface. In other aspects according to the present disclosure, the second jaw member includes a tissue engaging surface and the distal cam section of the second jaw member is disposed at an angle within the range of about 0 degrees to about 90 degrees relative to the tissue engaging surface. In still other aspects according to the present disclosure, the proximal cam section of the second jaw member is disposed at an angle within the range of about 0 degrees to about 90 degrees relative to the tissue engaging surface.

In aspects according to the present disclosure, the forceps further includes a knife selectively transitionable between the jaw members to sever tissue disposed between the first and second jaw members. In other aspects according to the present disclosure, the knife includes a slot defined therein, the slot configured to allow reciprocation of the knife about the pivot during translation thereof.

In aspects according to the present disclosure, the forceps includes a switch operably associated with the housing and in electromechanical cooperation with a source of electrosurgical energy, the switch allowing a user to selectively supply electrosurgical energy to the jaw members to effect a tissue seal. In yet other aspects according to the present disclosure, the forceps includes a rotating assembly configured to allow selective rotation of the end effector assembly about the longitudinal axis.

In accordance with aspects of the present disclosure, an end effector assembly for a forceps includes a first jaw member having a cam slot defined therein configured to receive a cam pin. The cam slot of the first jaw member includes a distal cam section and a proximal cam section, the distal cam section disposed at a first angle relative to a longitudinal axis defined through the end effector assembly and the proximal cam section disposed at a different angle relative to the longitudinal axis. A second jaw member includes a cam slot defined therein configured to receive the cam pin. The cam slot of the second jaw member includes a distal cam section and a proximal cam section, the distal cam section disposed at a first angle relative to the longitudinal axis and the proximal cam section disposed at a different angle relative to the longitudinal axis. A pivot is operably coupled to the first and second jaw members to facilitate pivotable motion therebetween.

Upon initial translation of the cam pin, the cam pin engages the distal cam section of the first jaw member causing the first jaw member to move relative to the second jaw member about the pivot while the cam pin engages the distal cam section of the second jaw member causing the second jaw member to remain stationary. Upon continued translation of the cam pin, the cam pin engages the proximal cam section of the first jaw member causing the first jaw member to remain stationary relative to the second jaw member while the cam pin engages the proximal cam section of the second jaw member causing the second jaw member to move relative to the first jaw member about the pivot to close against tissue disposed between the first and second jaw members.

BRIEF DESCRIPTION OF THE DRAWINGS

Various embodiments of the subject instrument are described herein with reference to the drawings wherein:

FIG. 1 is a right, perspective view of an endoscopic bipolar forceps showing a housing, a shaft and an end effector assembly according to the present disclosure;

FIG. 3A is a side, schematic view of the end effector assembly of FIG. 1 showing the first and second jaw members in a bilateral jaw position;

FIG. 3B is a side, schematic view of the end effector assembly of FIG. 1 showing the first and second jaw members in a unilateral jaw position; and FIG. 3C is a side, schematic view of the end effector assembly of FIG. 1 showing the first and second jaw members in a closed position.

DETAILED DESCRIPTION

Figure 2A:
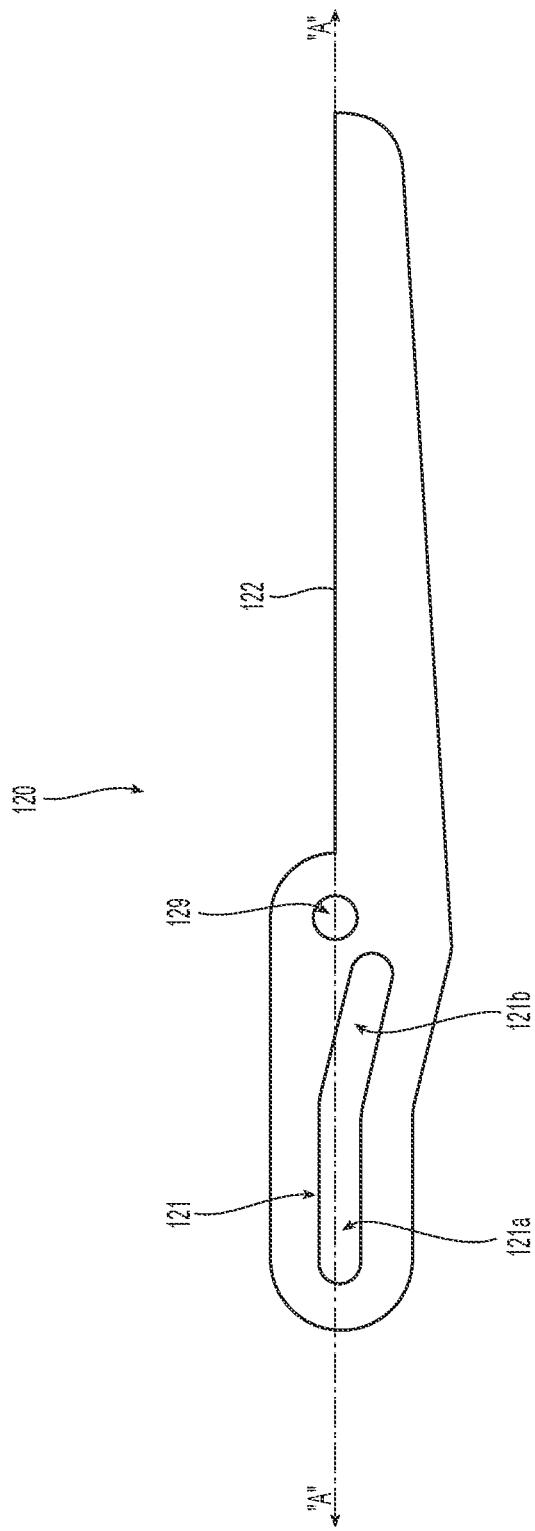
FIG. 2A is an enlarged, side view of a first jaw member of the end effector assembly.

Turning now to FIG. 1, one embodiment of an endoscopic bipolar forceps 10 is shown for use with various surgical procedures and generally includes a housing 20, a handle assembly 30, a rotating assembly 80, a trigger assembly 70 and an end effector assembly 100 which mutually cooperate to grasp, seal and divide tubular vessels and vascular tissue. Forceps 10 includes a shaft 12 which has a distal end 16 dimensioned to mechanically engage the end effector assembly 100 and a proximal end 14 which mechanically engages the housing 20. Details of how the shaft 12 connects to the end effector are not described in detail but may be found in U.S. Pat. No. 8,647,341 the entire contents of which is incorporated by reference herein.

The proximal end 14 of shaft 12 is received within the housing 20 and the connections relating thereto are described in detail with respect to the above-identified U.S. Pat. No. 8,647,341. Forceps 10 also includes an electrosurgical cable 310 which connects the forceps 10 to a source of electrosurgical energy, e.g., a generator (not shown). Generators such as those sold by Covidien—a division of Medtronic, may be used as a source of electrosurgical energy, e.g., FX8 Energy Platform, FT10 Energy Platform, ForceTriad™ Energy Platform, LS10 Generator, FORCE EZ™ Electrosurgical Generator, FORCE FX™ Electrosurgical Generator, FORCE 1C™, FORCE 2™ Generator, SurgiStat™ Low Energy Electrosurgical Generator. One such system is described in commonly-owned U.S. Pat. No. 6,033,399 entitled "ELECTROSURGICAL GENERATOR WITH ADAPTIVE POWER CONTROL" the entire contents of which are hereby incorporated by reference herein. Other systems have been described in commonly-owned U.S. Pat. No. 6,187,003 entitled "BIPOLAR ELECTRO-SURGICAL INSTRUMENT FOR SEALING VESSELS" the entire contents of which is also incorporated by reference herein.

Handle assembly 30 includes a fixed handle 50 and a movable handle 40. Fixed handle 50 is integrally associated with housing 20 and handle 40 is movable relative to fixed handle 50. Rotating assembly 80 is integrally associated with the housing 20 and is rotatable approximately 180 degrees in either direction about a longitudinal axis X-X defined through shaft 12.

Housing 20 is formed from two (2) housing halves 20a and 20b which each include a plurality of interfaces dimensioned to mechanically align and engage one another to form housing 20 and enclose the internal working components of forceps 10. As can be appreciated, fixed handle 50 which, as mentioned above, is integrally associated with housing 20, takes shape upon the assembly of the housing halves 20a and 20b. Movable handle 40 and trigger assembly 70 are typically made of unitary construction and are operatively connected to the housing 20 and the fixed handle 50 during the assembly process.

End effector assembly 100 is attached at the distal end 16 of shaft 12 and includes a pair of opposing jaw members 110 and 120. Movable handle 40 of handle assembly 30 is ultimately connected to a drive assembly (not shown) which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. Rotating assembly 80 allows selective rotation of the end effector assembly 100.

Turning now to the more detailed features of the present disclosure as described with respect to FIG. 1, movable handle 40 includes a finger loop 41 which has an aperture 42 defined therethrough which enables a user to grasp and move the handle 40 relative to the fixed handle 50. Handle 40 also includes an ergonomically-enhanced gripping element 43 disposed along the inner peripheral edge of aperture 42 which is designed to facilitate gripping of the movable handle 40 during activation. Gripping element 43 may include one or more protuberances, scallops and/or ribs to enhance gripping. Movable handle 40 is selectively moveable about one or more pivots (not shown) from a first position relative to fixed handle 50 to a second position in closer proximity to the fixed handle 50 which, as explained below, imparts movement of the jaw members 110 and 120 relative to one another.

As explained in more detail with respect to the above-identified U.S. Pat. No. 8,647,341, the movable handle 40 includes a clevis (not shown) that cooperates with the drive assembly (not shown) to impart movement of the jaw members 110, 120 relative to one another. The lower end of the movable handle 40 includes a flange 90 having a distal end (not shown) that rides within a predefined channel (not shown) disposed within fixed handle 50 to lock the movable handle 40 relative to the fixed handle 50.

End effector assembly 100 includes opposing jaw members 110, 120 which cooperate to effectively grasp tissue for sealing purposes. As explained in more detail below, end effector assembly 100 is designed as a combination unilateral and bilateral assembly meaning that during an initial range of movement, jaw member 120 moves from a bilateral jaw position (FIG. 3A) to a unilateral jaw position (FIG. 3B) while jaw members 110 remains stationary. Continued actuation of the drive assembly causes jaw member 110 to move unilaterally relative to jaw member 120 from the unilateral jaw position of FIG. 3A to a closed positon to grasp tissue (FIG. 3C).

FIG. 2A shows jaw member 120 of end effector assembly 100 which includes a tissue engaging surface 122 and a pivot hole 129 defined therein that is configured to receive a pivot pin 103 (FIG. 3A). Jaw member 120 also includes a cam slot 121 defined in a proximal end thereof that is configured to receive a cam pin 250 (FIG. 3A) that cooperates with a drive rod 190 of the drive assembly to impart movement of the cam pin 250 between a distal position and various more proximal positions as explained below. Cam slot 121 includes distal and proximal cam sections 121b, 121a which, when biased by the cam pin 250, move jaw member 120 relative to jaw member 110.

More particularly, when cam pin 250 is initially pulled proximally by drive rod 190 of drive assembly in distal cam section 121b, cam pin 250 biases jaw member 120 along a first path from a bilateral jaw position as shown in FIG. 3A to a unilateral jaw position shown in FIG. 3B. Continued movement of the cam pin 250 proximally transitions the cam pin 250 into proximal cam section 121a which maintains jaw member 120 in the unilateral jaw position as the cam pin 250 moves therein.

Figure 2B:
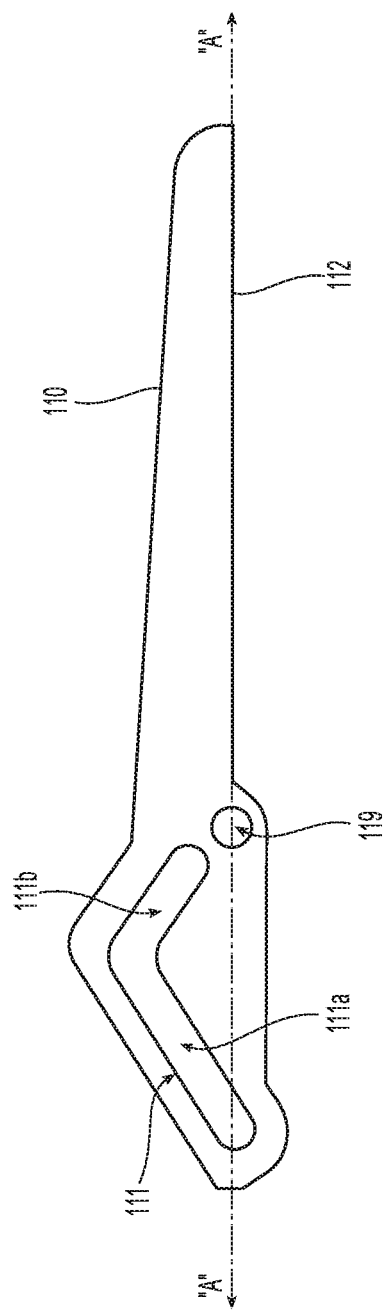
FIG. 2B is an enlarged, side view of a second jaw member of the end effector assembly.

FIG. 2B shows jaw member 110 of end effector assembly 100 which includes a tissue engaging surface 112 and a pivot hole 119 defined therein that is configured to receive the pivot pin 103 (FIG. 3A). Jaw member 110 also includes a cam slot 111 defined in a proximal end thereof that is configured to receive cam pin 250 (FIG. 3A) that cooperates with drive rod 190 of the drive assembly to impart movement of the cam pin 250 between a distal position and various more proximal positions as explained below. Cam slot 111 includes distal and proximal cam sections 111b, 111a which, when biased by the cam pin 250, move jaw member 110 relative to jaw member 120. More particularly, when cam pin 250 is initially pulled proximally by drive rod 190 of drive assembly in distal cam section 111b, jaw member 110 remains unbiased while jaw member 120 is moved to the unilateral jaw position shown in FIG. 3B. Continued movement of the cam pin 250 proximally transitions the cam pin 250 into proximal cam section 111a which maintains jaw member 120 in the unilateral jaw position as explained above and simultaneously biases jaw member 110 towards jaw member 120 as the cam pin 250 moves along proximal cam section 111a to close about tissue as shown in FIG. 3C.

FIGS. 3A-3C show actuation of the forceps 10 and movement of the end effector assembly 100 to approximate the jaw members 110, 120 about tissue. More particularly, as mentioned above, movement of handle 40 relative to handle 50 actuates the drive assembly to pull the drive rod 190 proximally in the direction of arrow "B". As the drive rod 190 is pulled proximally, the cam pin 250 rides within or proximate an elongated slot 186 defined within knife 185. As cam pin 250 is pulled proximally, cam pin 250 also rides within cam slots 111 and 121 to move jaw members 110, 120. Upon initial movement of the cam pin 250 within the distal cam sections 111b, 121b of jaw members 110, 120, respectively, jaw member 120 is moved from an unactuated or spaced apart, bilateral jaw positon (FIG. 3A) to a second, spaced apart unilateral jaw position (FIG. 3B), i.e., jaw member 120 moves relative to jaw member 110 while jaw member 110 remains stationary.

During this initial movement tissue may be oriented within the jaw members 110, 120. Continued movement of the drive rod 190 transitions cam pin 250 into cam sections 111a, 121a and moves jaw member 110 relative to jaw member 120 while jaw member 120 remains stationary and in the unilateral jaw position. Maintaining jaw member 120 in the unilateral jaw position while approximating tissue prevents the knife 185 from getting trapped during reciprocation thereof. Various knives or cutting mechanisms and how the knives connect to the trigger assembly 70 are described in the above-referenced, commonly-owned U.S. Pat. No. 8,647,341 the entire contents of which is incorporated by reference herein.

The cam sections 111a, 111b and 121a, 121b of each respective cam slot 111, 121 may be configured at various angles to control the movement of each jaw member 110, 120 when biased by drive rod 190. For example, during the range of motion, the angle of cam section 121b of cam slot 121 of jaw member 120 may vary within the range of about 0 degrees to about 90 degrees relative to a longitudinal axis A-A defined through end effector assembly 100 while the angle of cam section 121a is substantially parallel to the longitudinal axis A-A defined through end effector assembly 100 so that jaw member 120 remains in the unilateral jaw position when jaw member 110 closes about tissue. As such, the angle of cam section 121b of cam slot 121 may vary within the range of about 0 degrees to about 90 degrees relative to tissue engaging surface 122 (See FIG. 2A). Cam section 121a may vary within the range of about 0 degrees to about 90 degrees relative to tissue engaging surface 122 (See FIG. 2A).

The angle of cam section 111b of cam slot 111 of jaw member 110 is designed to maintain jaw member 110 in the bilateral jaw position as jaw member 120 transitions to the unilateral jaw position. During the range of motion and when jaw member 120 is moved from the bilateral jaw position to the unilateral jaw position, the angle of cam section 111b is substantially parallel to the longitudinal axis A-A of end effector assembly 100. As such the angle of cam section 111b may vary within the range of about 0 degrees to about 90 degrees relative to tissue engaging surface 122 (See FIG. 2B).

Once jaw member 120 transitions to the unilateral jaw position, cam section 111a is then engaged by drive rod 190 to bias jaw member 110 to close about tissue while jaw member 120 remain stationary due to cam section 121a being substantially parallel to longitudinal axis A-A. As such, the angle of cam section 111a of cam slot 111 may vary within the range of about 0 degrees to about 90 degrees relative to tissue engaging surface 112 (See FIG. 2B).

As mentioned above, the jaw members 110, 120 may be opened, closed and rotated to manipulate tissue until sealing is desired. This enables the user to position and re-position the forceps 10 prior to activation and sealing. The end effector assembly 100 is rotatable about longitudinal axis A-A through rotation of the rotating assembly 80. Trigger assembly 70 mounts atop movable handle 40 and cooperates with a knife assembly (not shown) to selectively translate the knife 185 through a formed tissue seal. A switch 200 is disposed atop housing 20 and is configured to permit the user to selectively activate the forceps 10. When switch 200 is depressed, electrosurgical energy is transferred to jaw members 110, 120, respectively and through tissue to form a tissue seal.

A safety switch or circuit (not shown) may be employed such that the switch 200 cannot fire unless the jaw members 110 and 120 are closed and/or unless the jaw members 110, 120 have tissue held therebetween. Various safety mechanisms and feedback systems are described in commonly-owned, U.S. Pat. No. 7,137,980 entitled "METHOD AND SYSTEM FOR CONTROLLING OUTPUT OF RF MEDICAL GENERATOR" the entire contents of which are hereby incorporated by reference herein.

Once the desired position for the sealing site is determined and the jaw members 110, 120 are properly positioned, handle 40 may be compressed to initially orient tissue between jaw members 110, 120 as jaw member 120 moves to the unilateral jaw position. Once oriented, handle 40 may be further compressed to close jaw member 110 about tissue. When closed, cam pin 250 is biased against the proximal-most inner periphery of cam sections 111a and 121a to apply the necessary closure pressure to tissue within a range of about 3 kg/cm$^2$ to about 15 kg/cm$^2$. Flange 90 may be configured to lock handle 40 relative to handle 50 as explained in detail with respect to the above-referenced, commonly-owned U.S. Pat. No. 8,647,341 the entire contents of which is incorporated by reference herein. Once locked (or fully compressed and held), jaw members 110, 120 are fully compressed about the tissue and forceps 10 is now ready for selective application of electrosurgical energy via switch 200 and subsequent separation of the tissue via advancement of the knife 185 along direction of arrow "C".

One or both jaw members, e.g., jaw member 120, may include a stop member (not shown) which limits the movement of the two opposing jaw members 110, 120 relative to one another. The stop member extends from the sealing surface 122 a predetermined distance according to the specific material properties (e.g., compressive strength, thermal expansion, etc.) to yield a consistent and accurate gap distance "G" during sealing. The gap distance between opposing sealing surfaces 112, 122 during sealing ranges from about 0.001 inches to about 0.006 inches and, preferably, between about 0.002 and about 0.003 inches. As energy is being selectively transferred to the end effector assembly 100, across the jaw members 110, 120 and through the tissue, a tissue seal forms. Once formed, the knife 185 may be advanced (see arrow "C") to divide the tissue along the tissue seal. By initially orienting tissue between the jaw members 110, 120 when jaw member 120 moves from the bilateral jaw position to the unilateral jaw position, and then closing jaw member 110 on tissue while jaw member 120 remains stationary in the unilateral jaw position, the knife 185 does not become trapped between the jaw members 110, 120.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416 (now U.S. Pat. No. 8,828,023), and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. For example, although shown as a pull to close end effector assembly (i.e., drive rod 190 is pulled to close jaw members 110 and 120), it is contemplated that a push to close end effector assembly may be utilized to accomplish the same purpose (i.e., drive rod 190 may be pushed distally to close jaw members 110 and 120). Therefore, the above description should not be construed as limiting, but merely as exemplifications of particular embodiments. Those skilled in the art will envision other modifications within the scope and spirit of the claims appended hereto.

What is claimed is:

1. An endoscopic bipolar forceps, comprising:
   a housing;
   a shaft extending from the housing having an end effector assembly disposed at a distal end thereof and defining a longitudinal axis defined therethrough, the end effector assembly including:
      a first jaw member including a cam slot defined therein, the cam slot of the first jaw member including a distal cam section and a proximal cam section, the distal cam section disposed at a first angle relative to the longitudinal axis and the proximal cam section disposed at a different angle relative to the longitudinal axis;
      a second jaw member including a cam slot defined therein, the cam slot of the second jaw member including a distal cam section and a proximal cam section, the distal cam section disposed at a first angle relative to the longitudinal axis and the proximal cam section disposed at a different angle relative to the longitudinal axis; and
      a pivot operably coupled to the first and second jaw members to facilitate pivotable motion therebetween;
   a movable handle operably coupled to a drive rod configured to translate a cam pin within the cam slots of the first and second jaw members, wherein:
      upon initial actuation of the movable handle relative to the housing, the cam pin engages the distal cam section of the first jaw member causing the first jaw member to move relative to the second jaw member about the pivot while the cam pin engages the distal cam section of the second jaw member causing the second jaw member to remain stationary, and
      upon continued actuation of the movable handle relative to the housing, the cam pin engages the proximal cam section of the first jaw member causing the first jaw member to remain stationary relative to the second jaw member while the cam pin engages the proximal cam section of the second jaw member causing the second jaw member to move relative to the first jaw member about the pivot to close against tissue disposed between the first and second jaw members.

2. An endoscopic bipolar forceps according to claim 1, wherein upon initial actuation of the movable handle, the first jaw member is moved from a bilateral jaw position to a unilateral jaw position.

3. An endoscopic bipolar forceps according to claim 2, wherein when the second jaw member is disposed in the initial bilateral position, the distal cam section of the second jaw member is substantially parallel to the longitudinal axis.

4. An endoscopic bipolar forceps according to claim 2, wherein when the first jaw member is disposed in the unilateral position, the proximal cam section of the first jaw member is substantially parallel to the longitudinal axis.

5. An endoscopic bipolar forceps according to claim 1, wherein actuation of the movable handle pulls the cam pin proximally.

6. An endoscopic bipolar forceps according to claim 1, wherein the first jaw member includes a tissue engaging surface and the distal cam section of the first jaw member is disposed at an angle within the range of about 0 degrees to about 90 degrees relative to the tissue engaging surface.

7. An endoscopic bipolar forceps according to claim 1, wherein the first jaw member includes a tissue engaging surface and the proximal cam section of the first jaw member is disposed at an angle within the range of 0 degrees to about 90 degrees relative to the tissue engaging surface.

8. An endoscopic bipolar forceps according to claim 1, wherein the second jaw member includes a tissue engaging surface and the distal cam section of the second jaw member is disposed at an angle within the range of 0 degrees to about 90 degrees relative to the tissue engaging surface.

9. An endoscopic bipolar forceps according to claim 1, wherein the second jaw member includes a tissue engaging surface and the proximal cam section of the second jaw member is disposed at an angle within the range of 0 degrees to about 90 degrees relative to the tissue engaging surface.

10. An endoscopic bipolar forceps according to claim 1, further compromising a knife selectively transitionable between the jaw members to sever tissue disposed between the first and second jaw members.

11. An endoscopic bipolar forceps according to claim 10 wherein the knife includes a slot defined therein, the slot configured to allow reciprocation of the knife about the pivot during translation thereof.

12. An endoscopic bipolar forceps according to claim 1 further comprising a switch operably associated with the housing and in electromechanical cooperation with a source of electrosurgical energy, the switch allowing a user to selectively supply electrosurgical energy to the jaw members to effect a tissue seal.

13. An endoscopic bipolar forceps according to claim 1 further comprising a rotating assembly configured to allow selective rotation of the end effector assembly about the longitudinal axis.

14. An end effector assembly for a forceps, comprising:
   a first jaw member including a cam slot defined therein configured to receive a cam pin, the cam slot of the first jaw member including a distal cam section and a proximal cam section, the distal cam section disposed at a first angle relative to a longitudinal axis defined through the end effector assembly and the proximal cam section disposed at a different angle relative to the longitudinal axis;
   a second jaw member including a cam slot defined therein configured to receive the cam pin, the cam slot of the second jaw member including a distal cam section and a proximal cam section, the distal cam section disposed at a first angle relative to the longitudinal axis and the proximal cam section disposed at a different angle relative to the longitudinal axis; and a pivot operably coupled to the first and second jaw members to facilitate pivotable motion therebetween, wherein upon initial translation of the cam pin, the cam pin engages the distal cam section of the first jaw member causing the first jaw member to move relative to the second jaw member about the pivot while the cam pin engages the distal cam section of the second jaw member causing the second jaw member to remain stationary, and upon continued translation of the cam pin, the cam pin engages the proximal cam section of the first jaw member causing the first jaw member to remain stationary relative to the second jaw member while the cam pin engages the proximal cam section of the second jaw member causing the second jaw member to move relative to the first jaw member about the pivot to close against tissue disposed between the first and second jaw members.

* * * * *